United States Patent [19]

Hondeghem

[11]  4,255,790
[45]  Mar. 10, 1981

[54] PROGRAMMABLE PULSE GENERATING SYSTEM

[76] Inventor: Luc M. Hondeghem, 128 Caribe Isle, Novato, Calif. 94947

[21] Appl. No.: 945,585

[22] Filed: Sep. 25, 1978

[51] Int. Cl.³ .................................. G01R 13/20
[52] U.S. Cl. .................................. 364/487; 364/580; 364/413
[58] Field of Search ............... 364/579, 486, 487, 413, 364/580; 235/302; 307/416, 106; 324/121 R

[56] References Cited

U.S. PATENT DOCUMENTS

| | | | |
|---|---|---|---|
| 3,449,721 | 6/1969 | Dertouzos et al. | 364/900 |
| 3,659,087 | 4/1972 | Green et al. | 364/468 |
| 3,764,995 | 10/1973 | Helf, Jr. et al. | 364/579 X |
| 3,931,506 | 6/1976 | Borrelli et al. | 235/302 |
| 4,055,801 | 10/1977 | Pike et al. | 235/302 X |
| 4,065,664 | 12/1977 | Kristof et al. | 364/487 |
| 4,104,725 | 8/1978 | Rose et al. | 364/487 |
| 4,158,884 | 6/1979 | McKinley et al. | 235/302 X |

*Primary Examiner*—Edward J. Wise
*Attorney, Agent, or Firm*—Edward B. Gregg; Willis E. Higgins

[57] ABSTRACT

This system generates output pulses in successive periods of time, each including sub-intervals during which the output pulses may be varied in accordance with a pre-determined scheme. The time periods and sub-intervals within the periods are defined by means of signals derived from a fundamental clock frequency generation circuit and first and second parallel sets of frequency division circuits connected to the fundamental frequency generation circuit. The first set of frequency division circuits is used together with a sub-interval timing circuit to define the sub-intervals of time included in each period. A system control means is connected to the frequency generation and division circuits, the timing circuits, a means for entering information into the system defining the periods and sub-intervals and the characteristics of output waveforms to be produced in each sub-interval, and to a variable electrical signal generation means which produce the output waveforms in accordance with the information entered into the system. Since the time periods, sub-intervals and output waveforms are all variable in accordance either with a pre-determined scheme, or on a real time basis depending on response of a subject under test, this system may be used to generate complex strings of waveforms especially suitable for measuring responses of biological samples to stimulation by electrical signals in pharmacological, physiological and other biomedical applications.

10 Claims, 10 Drawing Figures

PROGRAMMABLE PULSE GENERATING SYSTEM

BACKGROUND OF THE INVENTION

1. Field of the Invention

This invention relates to a programmable waveform generating system especially adapted to produce strings of output pulses suitable for measuring the response of biological samples to electrical stimulation under different conditions. More particularly, it relates to such a system suitable for measuring responses of living tissue to electrical stimulation. Most especially, it relates to such a system in which the output pulses used to stimulate the living tissue may be easily varied by the user or by the system itself under suitable program control, depending on the response of the tissue to the waveforms.

2. Description of the Prior Art

The search for chemical substances exhibiting desirable pharmacological properties is complex and never ending. In many instances, this search is hampered by a lack of knowledge of the mechanism at the cellular or even molecular level by which a particular chemical substance produces desirable pharmacological effects.

An approach which has proved to be useful in understanding the mechanism by which a particular pharmacological compound produces its effects has been through applying electrical signals of living tissue and measuring the response of the tissue to these signals both in the absence and presence of a substance under study. This approach is often based on the fact that living tissue produces minute electrical signals which vary as the environment of the tissue is varied. This tissue may also produce observable physiological or biochemical (e.g. metabolic) responses to such electrical stimulation. In order to obtain meaningful information by such electrical stimulus of tissue, it is necessary to change the timing, voltage and current of such signals and study the differences in responses produced by the tissue. It is often then desirable to change the applied signals further on the basis of the responses received to pulses originally applied to the tissue.

Similar considerations apply generally in the biomedical field. Various responses of living tissue to different forms of electrical stimulation are of use in elucidating the mechanisms by which organisms function. When a set of pulses is used to stimulate living tissue, a pattern of responses will often follow an exponential relationship until a steady state response condition is reached. It is often desired to change the set of pulses applied to the tissue at different portions of the exponential response. Because the exact nature of the exponential response is often not known at the time of the beginning of a series of experiments, a system cannot be completely programmed ahead of time to produce the required set of pulses. In many cases, it is desired to stress an organism or tissue with a repeated set of pulses until a steady state response is obtained, apply a different set of pulses to test the organism or tissue at that time, apply new stressing pulses until another steady state response is obtained, apply new testing pulses, and so forth.

Primarily as a result of the need to test performance of electronic circuits, programmable pulse generators for supplying output pulses are known in the art. However, the requirements for such programmable pulse generators in electronic applications are quite different than are required for the study of living tissue. In the electronic field, pulse frequencies in the gigahertz range are common.

While a string of pulses at such high frequency may be fairly complex in the electronic field, once a pulse program for a particular circuit has been established, it usually does not need to be changed. As a result, typical programmable pulse generators for electronic applications rely on a so-called "test can" which includes specialized circuitry for generating a particular string of pulses. With this approach, a new test can must be provided each time the pulse string produced by the pulse generator is to be changed. Alternatively, a pulse string may be changed in prior art test equipment for electronic applications in certain respects by manual operator intervention, such as by setting decade switches and the like.

On the other hand, for biomedical research, lower maximum frequencies in the megahertz (MHz) range are sufficient in a pulse string. However, it is often desired to apply a multiplicity of pulse strings varied in one or more parameters sequentially to a sample. In fact, it is often desired to modify parameters of subsequent pulse strings based on the response received for the sample to earlier pulse strings. Using commercially available pulse generators intended for electronic test applications in the biomedical field is quite time consuming due to the difficulty of making such changes in the pulses produced with them.

SUMMARY OF THE INVENTION

Accordingly, it is an object of this invention to provide a system for producing electrical signals suitable for application to a biological sample, which signals can be varied during successive periods of time without intervention by a user.

It is another object of the invention to provide a system which generates output electrical waveforms especially suited for biomedical applications in a plurality of time periods, each including a pre-determined number of sub-intervals during which the waveforms may vary.

It is a further object of the invention to provide a programmable pulse generating system which can, without user intervention, provide output pulses during successive time periods, each including sub-intervals of time during which the output pulses may vary.

It is still another object of the invention to provide a system for generating output electrical signals in successive time periods including sub-intervals during which the output signals may vary in accordance with a pre-determined scheme and in which the circuits for defining the periods and sub-intervals are configured to allow the periods and sub-intervals to be precisely defined in length and be contiguous with each other.

It is yet another object of the invention to provide such a pulse generating system which may be programmed by a user without knowledge of a programming language and without providing a new circuit to produce a different set of output pulses.

It is still another object of this invention to provide such a programmable pulse generator in which the output pulses may be converted to analog form as output voltages which vary in accordance with the voltage levels of the output pulses.

It is a still further object of the invention to provide a programmable pulse generator which is able to establish on a real time basis the characteristics of a subsequent set of test pulses to be applied to a test subject based on responses to a previous set of pulses applied thereto, without requiring operator intervention.

The attainment of the foregoing and related objects may be achieved through use of the novel programmable pulse generator herein disclosed. Such a programmable pulse generating system in accordance with the invention includes means for generating waveforms during a plurality of time periods, each including sub-intervals during which the output pulses may vary. A waveform generation control means is connected to the waveform generating means for defining the characteristics of the output waveform during each sub-interval. Timing means is connected to the waveform generation control means for defining the time periods and sub-intervals. Means is provided for entering information into the system to define the time periods, sub-intervals and characteristics of the output waveform during each sub-interval. A system control means is connected to the information entering means, the timing means and the waveform generation means. In a preferred form of the invention, the timing means includes two sets of timing circuits which operate alternatively to produce time period and sub-interval defining signals during successive time intervals. The set of timing circuits not producing the defining signals during a given interval is conditioned during that interval to produce the defining signals during a succeeding interval. The system control means is desirably a microprocessor, such as a commercially available Z-80 microprocessor.

Such a system is implemented in an especially preferred form by providing the required circuits in digital form using transistor-transistor logic ($T^2L$) and $T^2L$ compatible circuits. The output waveforms may be in digital form or, through use of a suitable digital to analog (D/A) converter, in analog form. This system enables a string of output pulses with different characteristics in different time intervals to be provided, and it allows the output pulse strings to be changed rapidly by the controlling program on the basis of subject response, thus providing meaningful data in biomedical studies more rapidly.

The attainment of the foregoing and related objects, advantages and features should be more readily apparent to those skilled in the art after review of the following more detailed description of the invention, taken together with the drawings, in which:

DETAILED DESCRIPTION OF THE INVENTION

Figure 1:
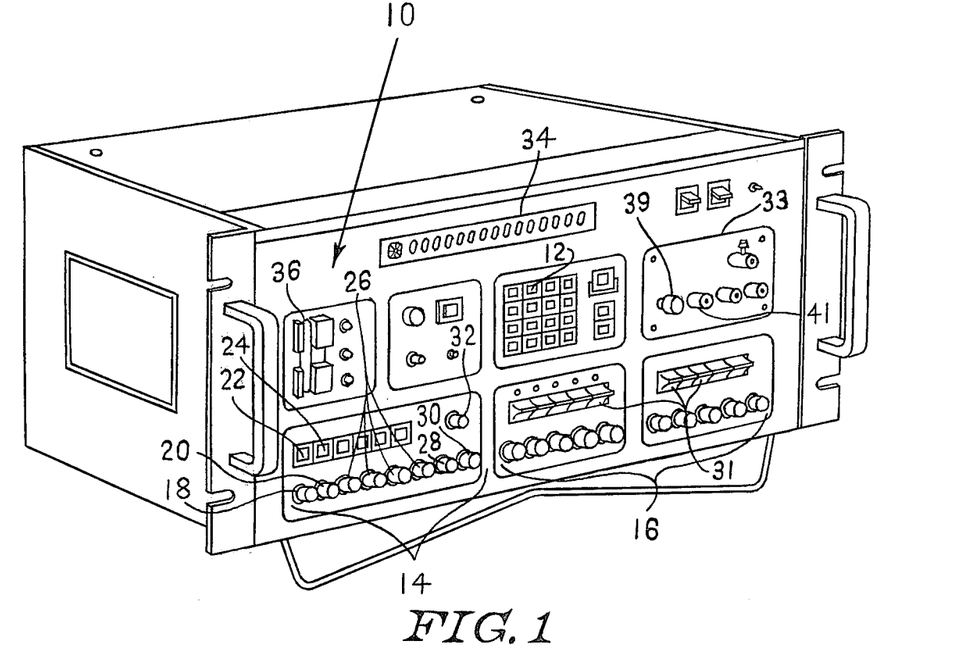
FIG. 1 is an external, perspective view of a system in accordance with the invention.

Turning now to the drawings, more particularly to FIG. 1, there is shown an external view of a system in accordance with the invention, including its control panel 10. The control panel includes a key pad 12 for entering information and programs into the system. A plurality of input jacks 14 is provided for supplying external signals to the system. A plurality of output jacks 16 furnishes the output waveforms from the system. The first two input jacks 18 and 20 may be used to provide external start and stop signals for the system, which also may be provided manually by the go and stop buttons 22 and 24 positioned immediately above the input jacks 18 and 20. The next four input jacks 26 are used to provide external sense signals to the system, typically obtained from a biological sample to which output signals from output jacks 16 are supplied or from manual inputs by the user based on observation. The remaining two input jacks 28 and 30 provide input signals to allow signal time periods and sub-intervals to be determined by external events, again typically produced by a biological sample under test or by any other external timing means. Jack 32 allows the fundamental clock frequency generated in the system to be provided as an output signal.

Output jacks 16 are provided in two sets of five each and provide the output pulse waveforms in the system. Each jack of a set is for a sub-interval of time within a time period as defined by the system. The output signals for sub-intervals of successive time periods are provided alternately by the two sets of output jacks 16, thus allowing conditioning of time circuits to gate the output signals to the jacks to be accomplished during a time interval in which that set of timing circuits is not gating the output signals. Switches 31 above the output jacks 16 allow individual control of the output jacks 16.

An alternative analog output section 33 is used when it is desired to convert the usual digital output signals from the system to an analog signal by means of a D/A converter. An intensity control 39 is also provided to allow manual selection of an analog signal to be supplied on jack 41. This control also allows analog control over duration since an A/D converter reads the number for duration from the potentiometer associated with control 39. An alphanumeric display panel 34 both provides an indication of numerical data entered into the system and is used to ask questions of a user in a human language, e.g. English. Responses to the questions entered via key pad 12 operate to program the instrument. A digital casette reader/recorder 36 allows programs and data to be entered into the system from a digital casette, allows programs and data entered by means of key pad 12 to be recorded on a digital casette, and allows an output pulse program to be stored on a casette for permanent storage as it is being run.

Figure 2:
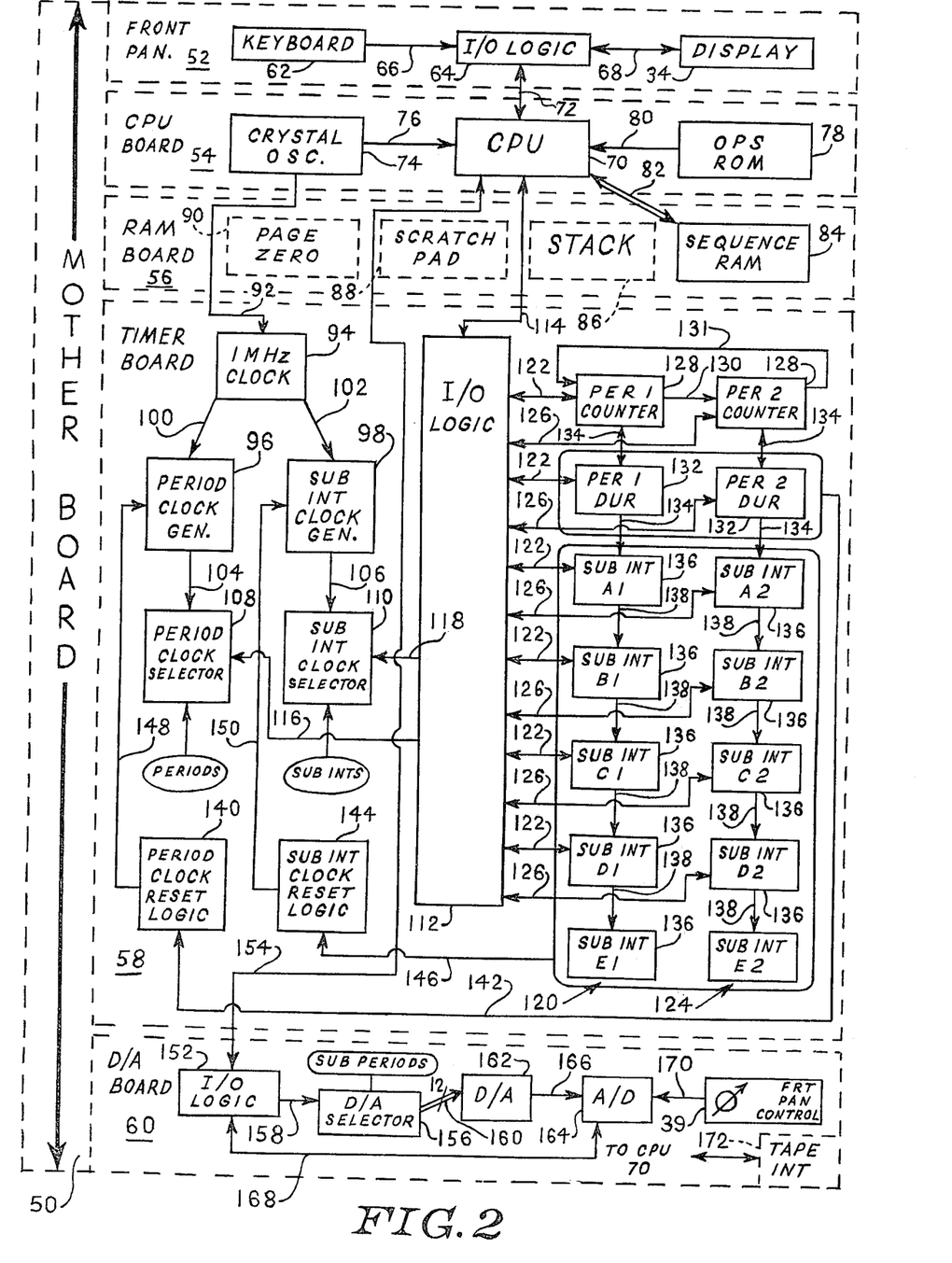
FIG. 2 is a block diagram of a system in accordance with the invention.

FIG. 2 shows the essential elements of a waveform generating system in accordance with the invention in block diagram form. The system includes a mother board 50, a front panel board 52 plugged into the mother board 50, a central processing unit (CPU) board 54, a random access memory (RAM) board 56, a timer board 58 and a D/A board 60, the latter boards all also being plugged into the mother board 50. The front panel board 52 includes a plurality of keyboard switches 62 responsive to key pad 12 (FIG. 1) and connected to input-output (I/O) logic circuits 64 as indicated at 66. The I/O logic circuits 64 interface between the keyboard switches 62 and display 34, as indicated at 68. The I/O logic circuit 64 also interfaces with CPU 70 on CPU board 54 as indicated at 72. A crystal oscillator 74 interfaces to CPU 70 as indicated at 76. A read only memory 78 containing an operating system program interfaces with the CPU 70 as indicated at 80. A plurality of data lines indicated at 82 connects the CPU 70 to a sequence random access memory 84 on RAM board 56, in which waveform sequence information is stored and retrieved in response to commands from CPU 70. Additional portions of the random access memory on RAM board 56 are assigned stack, scratch pad and page zero functions by the CPU 70 as indicated at 86, 88 and 90.

In addition to providing a fundamental frequency for CPU 70, crystal oscillator 74 also supplies its fundamental frequency on line 92 to a 1 MHz clock 94, i.e., a counter which divides down the fundamental frequency of oscillator 74 to 1 MHz. The 1 MHz frequency of clock 94 is further divided by period clock generator 96 and sub-interval clock generator 98, each connected to clock 94 by lines 100 and 102, respectively. The output frequencies of clock generators 96 and 98 are supplied on lines 104 and 106 to period frequency selector 108 and sub-interval frequency selector 110, respectively.

CPU 70 interfaces with I/O logic circuit 112 as indicated at 114. I/O logic circuit 112 supplies signals from the CPU 70 to the circuit elements on timer board 58. The I/O logic circuits 112 are connected to the period frequency selector 108 and the sub-interval frequency selector 110 by means of lines 116 and 118, respectively.

I/O logic circuits 112 are connected to a first set 120 of period and sub-interval counters by lines 122. Similarly, a second set 124 of period and sub-interval counters is connected to I/O logic circuits 112 by lines 126. Each set 120 and 124 of counters include period quantity counters 128 which count the number of repetitions of time periods incorporating a set of pulses during their sub-intervals, as will be explained in more detail in connection with FIGS. 4A and 4B. The two counters 128 are connected by line 130. Each set 120 and 124 of counters also includes a period duration counter 132, each connected to its corresponding period quantity counter 128 by line 134. Each of the period duration counters are connected to period clock reset logic circuits 140 as indicated by line 142. Similarly, each of the sub-interval counters 136 is connected to sub-interval clock reset logic 144 as indicated by line 146. The period clock reset logic circuit 140 is connected to period clock generator 96 by line 148, and the sub-interval clock reset logic circuit 144 is connected to the sub-interval clock generator 98 by line 150.

Turning now to the D/A board 60, I/O logic circuits 152, similar to the I/O logic circuits 112 on board 58, are connected to CPU 70 by line 154. I/O logic circuits 152 are in turn connected to D/A selection circuits 156 by line 158. The D/A selection circuits 156 are connected by twelve input lines 160 to a D/A converter 162, which converts digital signals on lines 160 to analog voltage levels.

In order to allow testing of the D/A converter 162 by CPU 70, the D/A converter 162 is folded back through an A/D converter 164 by means of lines 166 and 168 as shown. This feature allows the analog signals generated by D/A converter 162 to be converted back into digital form for comparison with the original digital signals supplied by the CPU in a test routine. Front panel intensity control 39 (see also FIG. 1) is also connected to A/D converter 164 by line 170. This control allows a user to obtain the function of an analog stimulator in a digital unit. Typically the user adjusts the intensity (current and voltage) of a pulse supplied via jack 41 (FIG. 1) so as to obtain a desired effect on a subject under test and then observes the value of the thus adjusted pulse after its conversion to digital form by the A/D converter 164 and transmission to display 34 via CPU 70.

Tape interface circuits 172 are also included on the D/A board 60 as well in order to provide more even distribution of circuit population on the boards and allow the CPU 70 to interface with casette tape unit 36 (FIG. 1).

Figure 3:
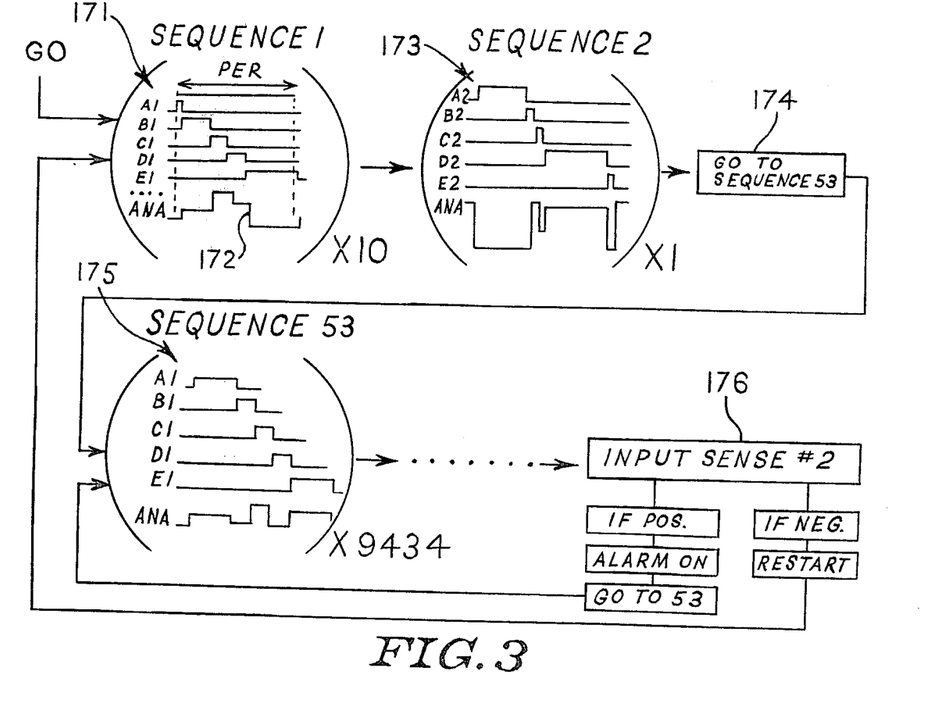
FIG. 3 is in part a diagram of a typical set of output waveforms to be produced with a system in accordance with the invention and in part a flow diagram carried out through use of a program in conjunction with the waveforms.

FIG. 3 represents a typical set of waveforms of the type to be produced using the system of this invention. Shown at 171 is a first sequence of pulses A1 through E1 occurring during successive sub-intervals of the period shown, together with an analog signal 172 produced from the A1–E1 signals by D/A converter 162 in FIG. 2. The designation X10 appearing as a subscript for the first sequence is to be repeated ten times. This means that the first set 120 of period and sub-interval counters shown in FIG. 2 would maintain control during the ten repetitions of the first pulse sequence. This first pulse sequence repeated ten times would typically be for the purpose of conditioning an organism or tissue under test to arrive at a steady state response condition. A second sequence of pulses is shown at 173. The subscript designation XI means that this second pulse sequence is only to be presented once. This second sequence of pulses 173 would therefore typically be used to test a living organism or tissue to which the first sequence of pulses 171 had been applied for pre-conditioning. Depending on results obtained with the second sequence of pulses 173, a user program might select from one or more additional pulse sequences for presentation to the subject under test. This is indicated by the if positive go to sequence 53 instruction at 174. Sequence 53 presents another set of pulses 175 to the subject under test. As indicated by the subscript, this set of pulses 175 is presented to the subject under test 9,434 times. As indicated at 176, a user program may incorporate a decision block to allow the sequence 53 pulses 175 to be presented the full 9,434 times if proper responses are being received from the subject. If not, the pre-conditioning pulses 171 of sequence one can be repeated until the subject under test is responding properly. From this example, it can be seen that the system of this invention can provide both highly complex and variable pulse sequences in accordance with a user program incorporating branching decisions.

Figures 4, 4A:
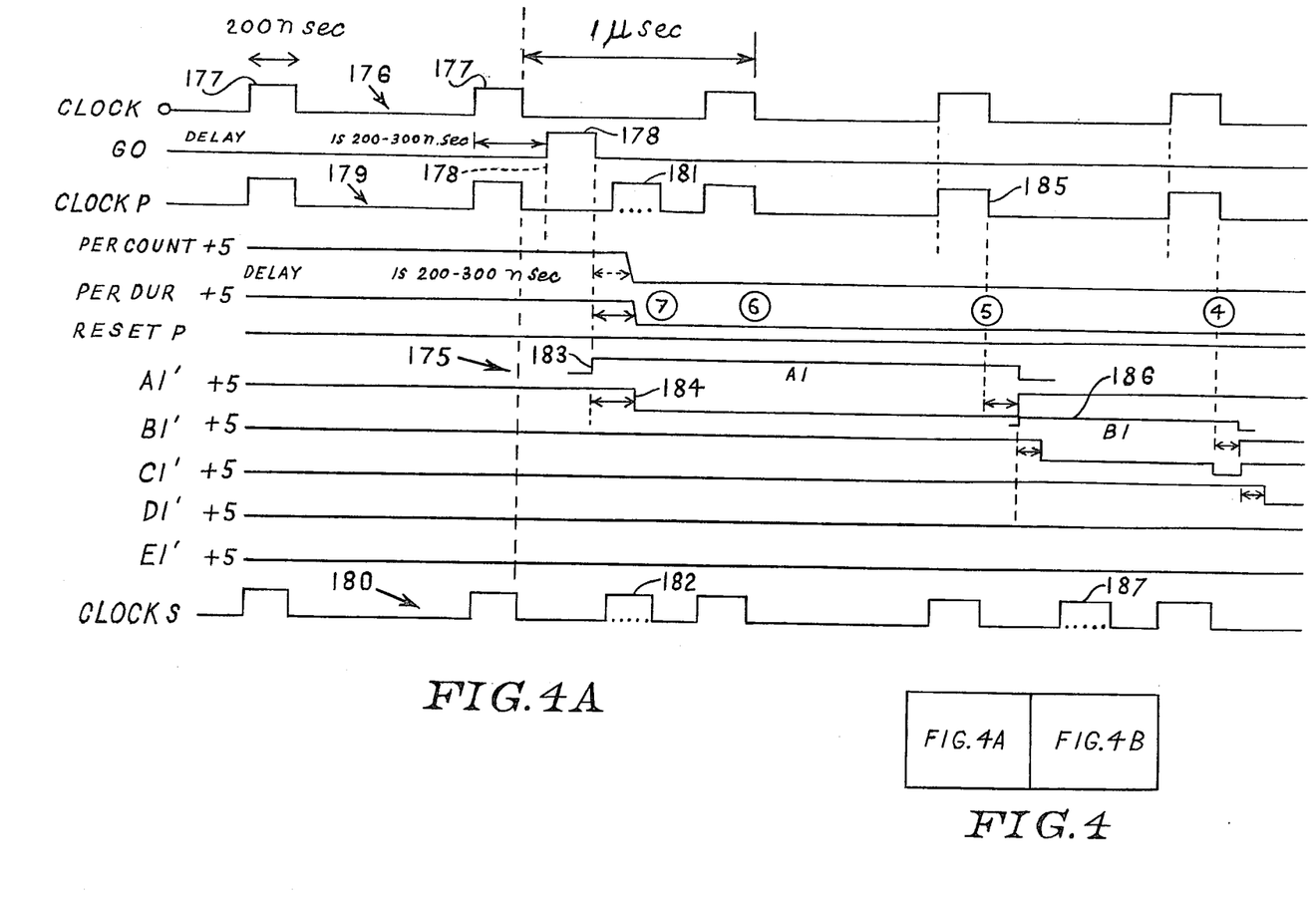
FIG. 4 shows the relationship between FIGS. 4A and 4B.
FIGS. 4A and 4B are diagrams of certain control pulses used in a system in accordance with the invention to produce output waveforms.
Figure 4B:
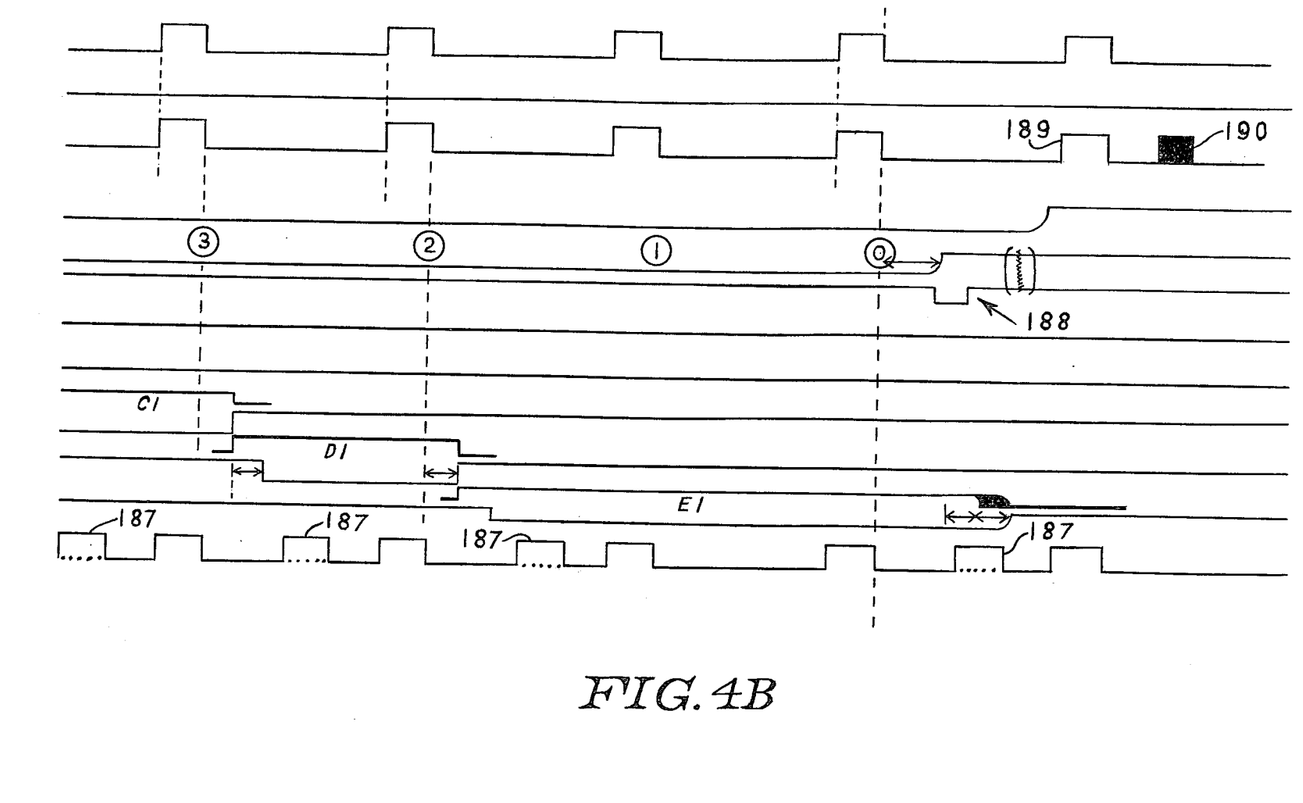

FIGS. 4A and 4B show a pulse program which enables the system to generate a set of waveforms 175 as shown in FIG. 3. The pulse program will be explained in detail with reference to the more detailed system and circuit diagrams which follow. Shown at 176 are the clock pulses having a period from trailing edge to trailing edge of 1 microsecond. Each of the pulses 177 as shown have a duration of 200 nanoseconds, obtained through use of a one shot circuit. Shown at 178 is a negative incursion in a normally inhibiting signal. This negative incursion 178 is produced as an initialization pulse when the system is started up and provides the starting point of reference for the subsequent pulses. Additional clock signals as shown at 179 and 180 are provided in order to allow the timing and counting of time periods in which the individual output pulses 175 are provided. In this example, the time period is 7 microseconds in duration, the A sub-interval is 2 microseconds in duration, sub-intervals B through D are 1 microsecond in duration and sub-interval E is 2 microseconds in duration. The additional clock pulse 179 is used to define the period. The additional set of clock pulses at 180 defines and counts the sub-intervals. Because the period and each sub-interval in this example are measured in microseconds, the clock pulses at 179 and 180 are identical to the master clock pulses 176.

Returning now to the section of FIG. 2 including the timing circuits which generate signals to indicate the time periods, the timer section includes first and second strings 120 and 124 of counters, which alternately produce output pulses during alternate periods as defined by the first and second period counters 128. The counter strings 120 and 124 also each include a period duration counter 132 with an output 138 connected to A1 and A2 sub-interval counters 136. A1 and A2 sub-interval counters 136 are connected to B1 and B2 sub-interval counters 136 by outputs 138. In like manner, B1 and B2 sub-interval counters 136 are connected to C1 and C2 sub-interval counters 136 by output 138, and so forth.

In operation, a timing sequence is initiated either by a GO signal on line 122 or a signal on line 131 indicating that a period defined by second period counter 128 has terminated. Either signal commences a period defined by first period counter 128. Simultaneously, this signal is supplied to period 1 duration counter 132 and to A1 sub-interval counter 136. At the conclusion of the A1 sub-interval, a signal on A1 sub-interval counter 136 output line 138 initiates the B1 counter sub-interval 136 to define the B1 sub-interval. This same sequence of operation continues through completion of the E1 sub-interval. It should be noted that, in practice, sub-intervals A1 through D1 are defined in accordance with data previously entered into the system. Interval E1 is determined as the remainder of the period defined by first period counter 128 after completion of sub-interval A1–D1. Entry of data to define the E1 sub-interval is therefore not necessary. At the conclusion of a period defined by first period counter 128 a signal on line 130 initiates count by second period counter 128 of the subsequent period defined by it. As in the case of the first period, the second period is broken up into five sub-intervals, each defined successively by the A2 through E2 sub-interval counters 136 as above. At the conclusion of this second period, a signal on line 131 initiates another period, measured by first period counter 128. Providing separate period counters, each with an associated set of sub-interval counters in this manner allows transparent updating of the period and sub-interval information during a period in which the other period counter and its associated sub-interval counters are controlling the definition of the time period and its sub-intervals. It should be noted that one of the period counters 128 will maintain control during repetition of the same pulses in subsequent time periods, such as for repetition of first pulse sequence 171 for 10 times, as indicated in FIG. 3.

Figure 5:
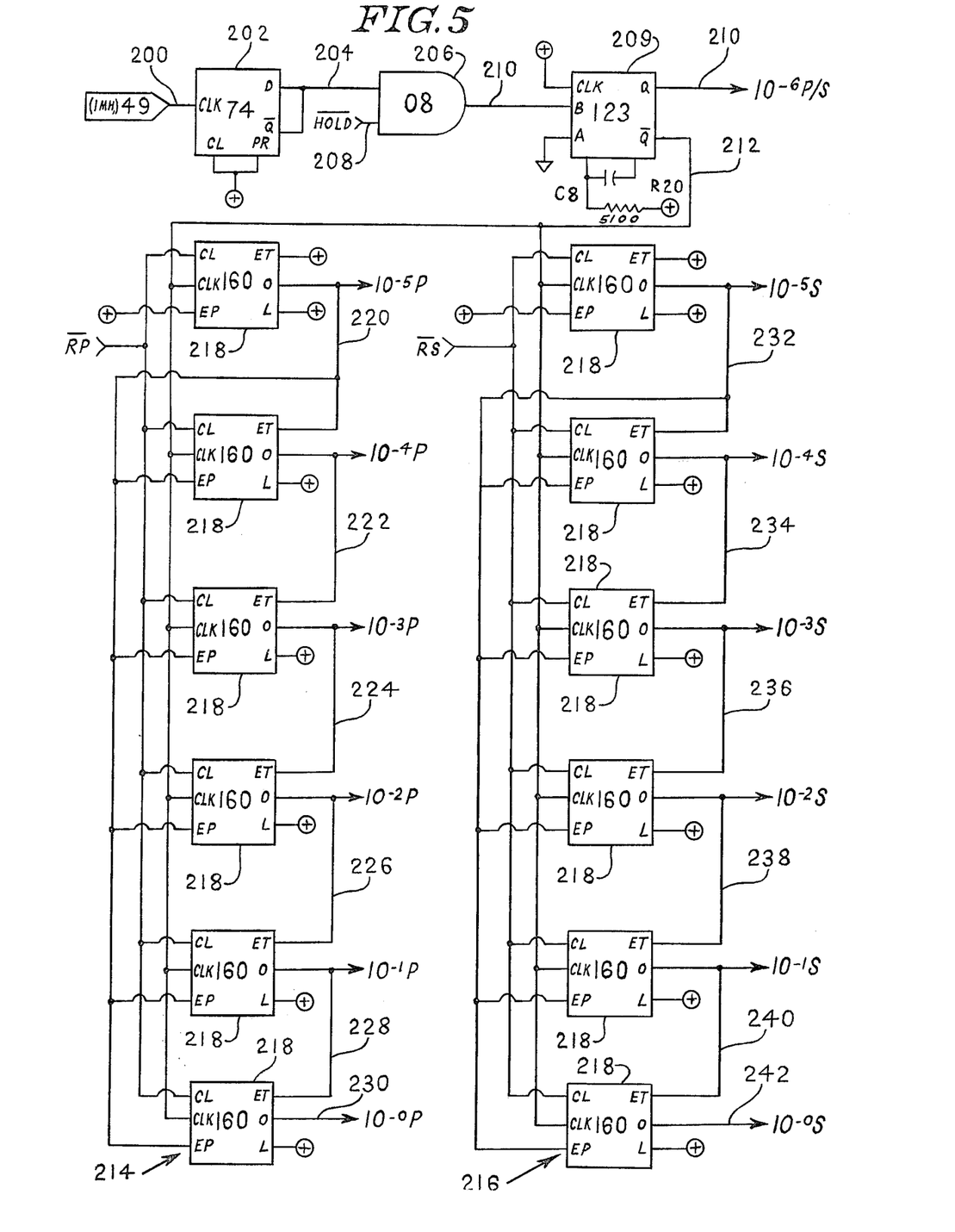
FIG. 5 is a block diagram of a portion of the system shown in FIG. 2.

Turning now to FIG. 5, a frequency division network suitable for providing sets of pulses which are combined to define the periods and sub-intervals is shown. In this and subsequent figures, the numbers in some of the circuit blocks refer to commercially available integrated circuit types. For example, the designation 123 inside block 209 refers to a 74LS123 type one shot circuit. The frequency division network is set up to establish a 1 MHz clock signal output from a 2 MHz input at 200. The 1 MHz clock signal is then divided in six successive stages to give the frequency used to define the periods and sub-intervals discussed above. The 2 MHz input at 200 is first divided by two by flip-flop 202 to produce a 1 MHz signal on line 204. This signal forms one input of AND gate 206. The other input 208 to AND gate 206 is for a $\overline{HOLD}$ signal. The presence of a $\overline{HOLD}$ signal on line 208 allows a 1 Mhz signal to pass AND gate 206 and be supplied to one shot circuit 209 on line 210. When a $\overline{HOLD}$ signal is low, all counters will be stopped at a particular point. When the $\overline{HOLD}$ signal is high, counting will resume at that particular point. The one shot circuit 209 converts 1 MHz square wave pulses to 200 nanosecond pulses at the same frequency, which are supplied as an output on line 210 (corresponding to clock pulses 177 in FIG. 4) and are also supplied on line 212 for further division to provide the period and sub-interval frequencies.

The 1 MHz signal on line 212 is divided down in decades from $10^{-6}$ to $10^0$ in two parallel strings 214 and 216 of dividers 218. The counters 218 are synchronous four-bit decade counters of the 74LS160 type, with the outputs 220, 222, 224, 226 and 228 of the counters in string 214 serving as an input to the counter 218 immediately below that output. Output 230 provides the lowest frequency in the string. In a similar manner, the outputs 232, 234, 236, 238 and 240 interconnect the counters 218 of sub-interval counter string 216. The lowest frequency from string 216 is provided on output 242.

Figure 6:
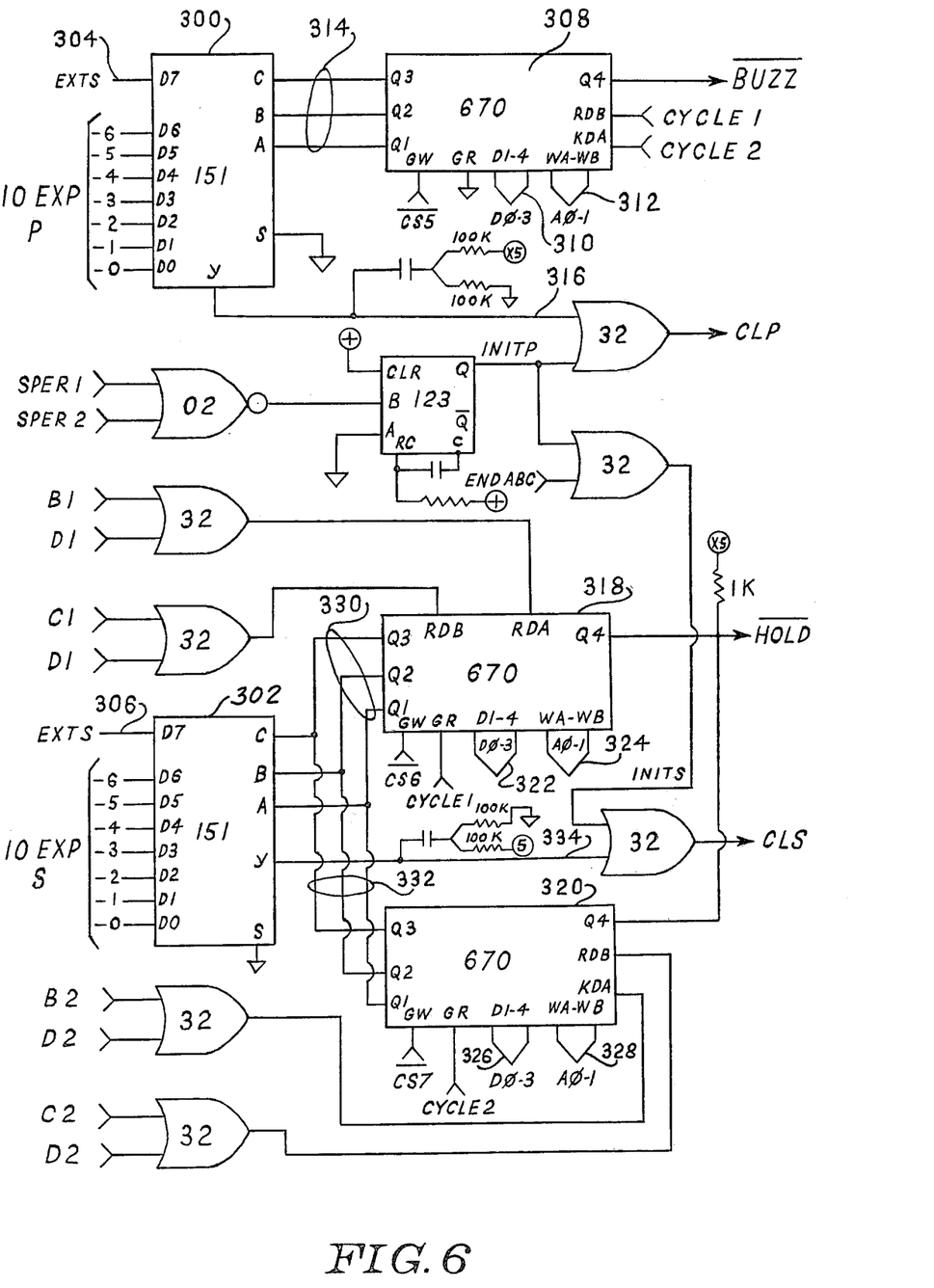
FIG. 6 is a schematic diagram of a portion of the system shown in FIG. 2.

FIG. 6 shows the circuits which provide the signals to define the periods and sub-intervals from the output frequencies generated by the circuitry of FIG. 5. As shown, output 210 and outputs 220–230 in FIG. 5 form inputs to a period data selection and multiplexer integrated circuit 300. Output 210 and outputs 232–242 in FIG. 5 form similar inputs to a sub-interval data selection and multiplexer integrated circuit 302. Input 304 to period selector 300 allows the period to be determined by counting external events. A similar input 306 to sub-interval selector 302 allows the sub-intervals to be determined by counting external events as well.

The period selection is accomplished by use of data stored in a random access memory 308, which has itself received the data from the Z-80 microprocessor CPU 70 (FIG. 2) on inputs 310 and 312. Appropriate signals for the selection are supplied from random access memory 308 to period selector 300 on lines 314. Signals defining the selection period are generated from the inputs on lines 210 and 220–230 and supplied on output 316 from period selector 300.

Sub-interval selection occurs in a similar manner through use of sub-interval selector 302, but under alternate control of random access memories 318 and 320. The random access memories 318 and 320 provide the information for defining the sub-intervals alternately in order to allow update of them during a period in which they are not providing the information to define the sub-intervals. As in the case of random access memory 308, the information is provided to random access memory 318 on inputs 322 and 324 and to random access memory 320 on inputs 326 and 328 from the Z-80 microprocessor CPU 70 (FIG. 2). The appropriate sub-interval information is supplied to sub-interval selector 302 on line 330 or 332, depending on which random access memory 318 or 320 is providing the information. Appropriate signals for defining the sub-intervals are generated from the inputs on lines 210 and 232–240 and supplied by sub-interval selector 302 on line 334.

Figure 7:
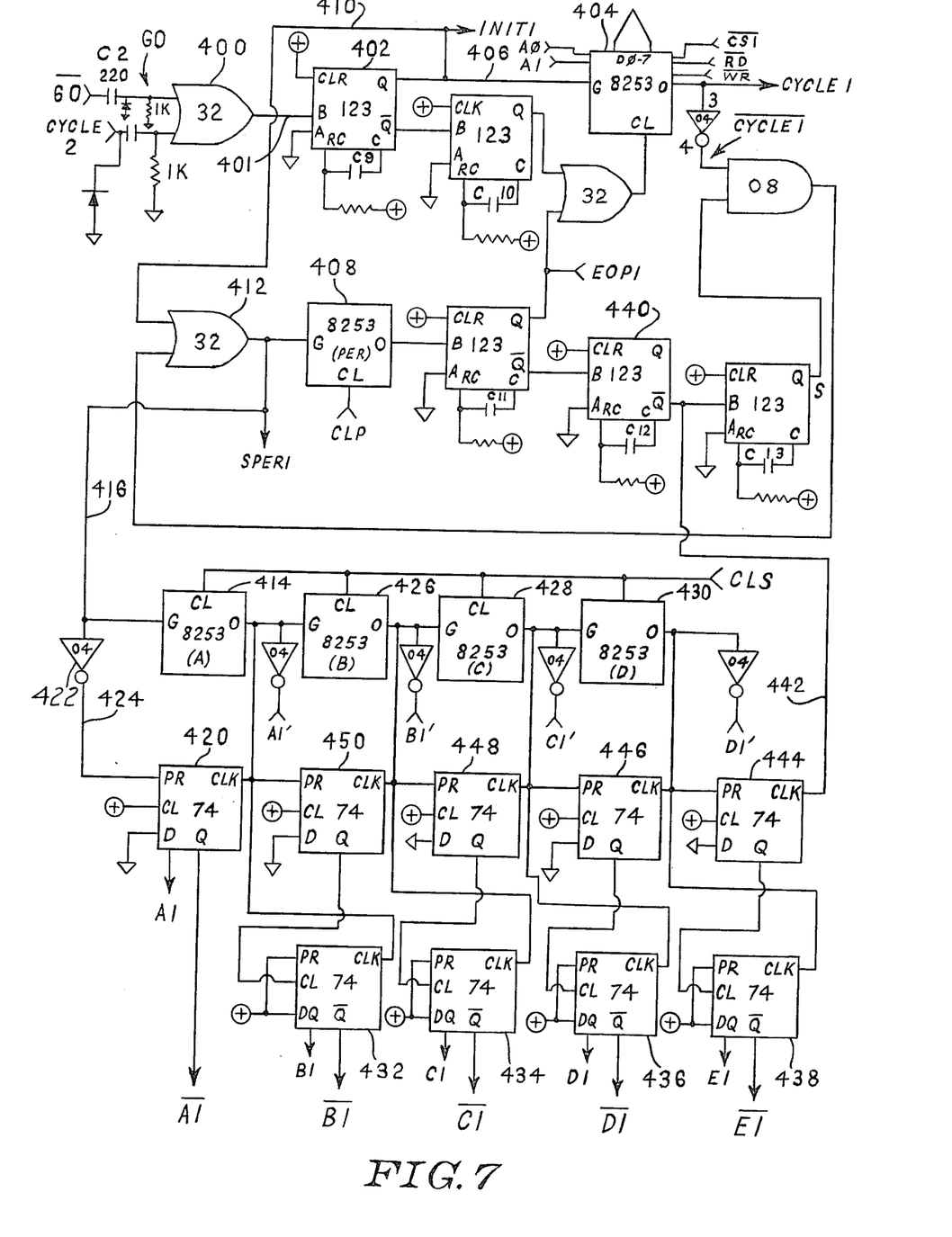
FIG. 7 is another schematic diagram of a portion of the system shown in FIG. 2.

FIG. 7 is a more detailed circuit diagram of one string 120 of the period and sub-interval counters in the block diagram of FIG. 2. It should be recognized that the other string 124 of the period and sub-interval counters in FIG. 2 is essentially a duplicate of what is shown in FIG. 7, and it therefore will not be presented in detail.

The circuit of FIG. 7 receives either a negative incursion in a $\overline{GO}$ signal or a similar CYCLE 2 signal from the other string 124 of period and sub-interval counters by AC coupling at OR gate 400. The AC coupled signal is supplied on line 401 to one shot circuit 402 to produce the standardized 200 ns. INIT pulse 178 (FIG. 4A). The INIT pulse 178 is supplied simultaneously to cycle counter 404 on line 406 to serial counter 408 on line 410 through OR gate 412, to sub-interval A counter 414 on line 416, and to positive edge triggered flip-flop 420 via inverter 422 and line 424. Using the INIT pulse to trigger counters 404, 408, and 414 and to trigger flip-flop 420 virtually simultaneously makes delays in the counters transparent to the user. This same concept is used for simultaneously triggering B, C and D sub-interval counters 426, 428 and 430 and their associated B1, C1, D1 flip-flops 432, 434 and 436 by the output of the previous counter 414, 426 or 428. A similar approach triggers the E1 flip-flop 438, but it does not have an associated sub-interval counter because the E1 sub-interval is defined as the rest of the time period after the sub-intervals A1–D1 have been subtracted from it. An appropriate signal from delay element one shot 440 on line 442 is rippled through flip-flops 444, 446, 448 and 450, also to insure the contiguity of output pulses A1–E1. In addition to providing contiguous output pulses during sub-intervals A through E of a time period, because the E pulse is defined as the remainder of subtracting the A through D sub-interval from the time period, the E sub-interval has tremendous range (e.g., one year) with microsecond resolution. Use of both strings 120 and 124 (FIG. 2) of period counters in this manner allows the E sub-interval to be very precisely placed at some time in the future (e.g., two years) as well. If one of the sub-intervals is made longer than its time period, the result can be interleaved output pulses, one from each string 120 and 124.

In order to avoid losing certain clock pulses in the time period clock pulse string 179 and the sub-interval clock pulse string 180 due to delays in the counter circuits 404, 408, 414, etc. it is necessary to add in extra pulses to the clock pulse strings as shown at 181, 182, 187 and 190 in FIGS. 4A and 4B to make up for actual clock pulses that would otherwise be missed. This can be done either by software control or by hard wired circuits.

Figure 8:
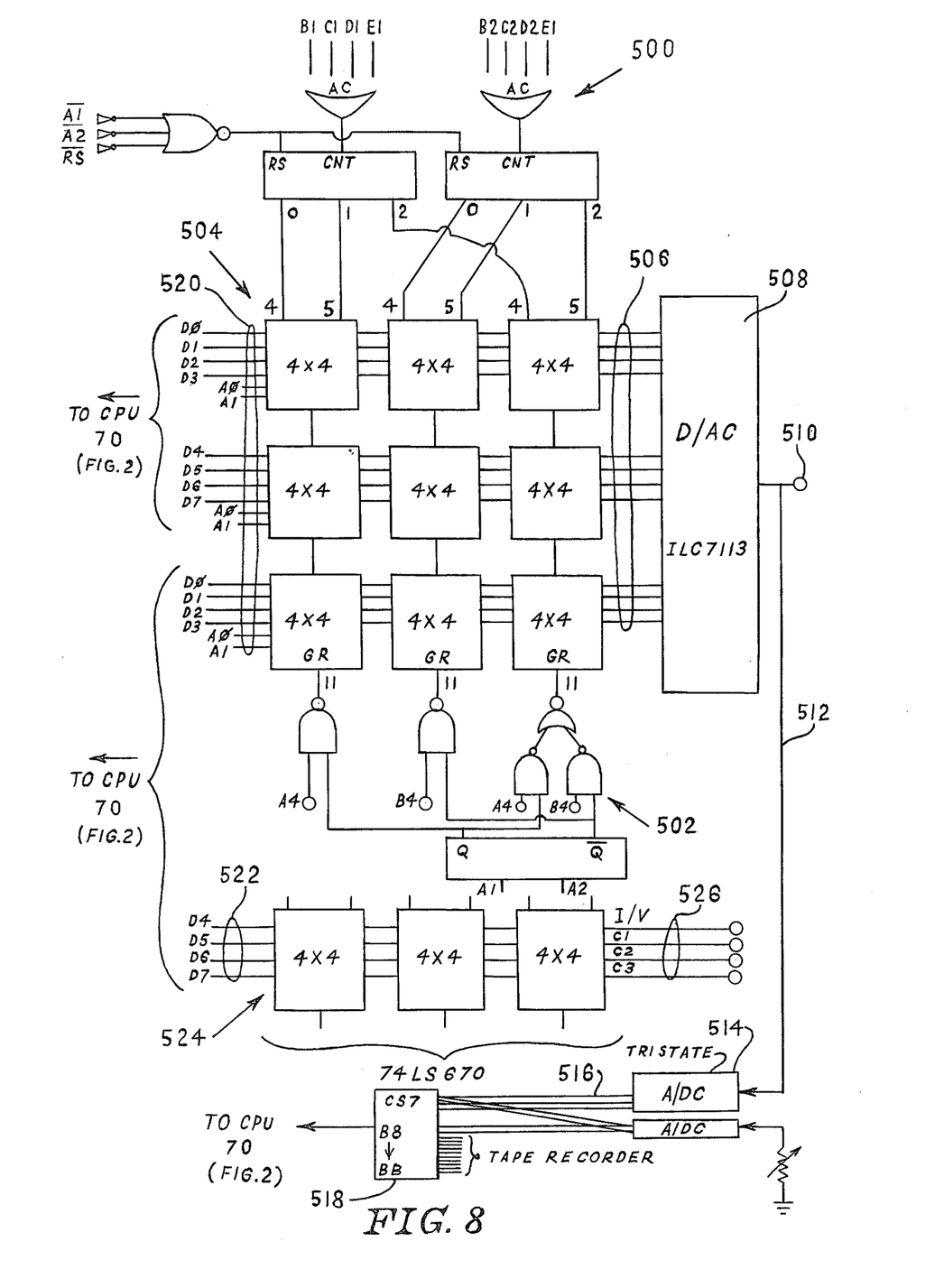
FIG. 8 is a third schematic diagram of another part of the system shown in FIG. 2.

FIG. 8 is a more detailed representation of the circuits on D/A board 60 in FIG. 2. I/O logic circuits 152 in FIG. 2 correspond to sub-interval decode circuits 500 and alternate cycle decode circuits 502. D/A selector circuits 156 in FIG. 2 correspond to memory array 504 in FIG. 8, which is made up of 74LS670 type memory integrated circuits. In response to appropriate control signals from decode circuits 500 and 502, the memory circuits 504 gate pulse information on lines 506 from which D/A converter 508 generates an analog output signal supplied at 510, for example analog signal 172 in FIG. 3. To allow self-testing of the D/A converter 508, line 512 supplies the analog signal to an analog to digital (A/D) converter 514 for reconversion to digital form. Output 516 supplies the resulting digital signal to interface circuit 518, which is in turn connected to CPU 70 for comparison of the reconverted digital signal with the original digital pulse information as supplied on lines 506.

It should be noted that there are twelve inputs 520 from the CPU 70 to memory circuits 504. Assuming use of an eight-bit Z-80 microprocessor, two eight-bit wide inputs from the CPU 70 are required to furnish the twelve inputs 520. The extra four inputs from the two eight-bit wide inputs can be supplied as inputs 522 to a second group of memory circuits 524 for generation of additional output signals at 526.

It should now be apparent that a programmable pulse generator capable of achieving the stated objects has been provided. This system provides output pulses in a plurality of time periods of essentially any duration, each sub-dividable into sub-intervals of lesser duration than the time periods. Successive time periods and intervals may be varied on a real time basis, without intervention by a user if desired. The time periods and intervals are precisely defined in length and are contiguous with each other. While these characteristics of the subject system make it especially desirable for producing electrical signals suitable for application to biological samples, especially for collision, summation, inhibition and facilitation studies in neurobiology, this programmable pulse generator should find application in a wide variety of other fields as well.

It should further be apparent to those skilled in the art that various changes in form and details may be made in the system as described. It is intended that such changes be included within the spirit and scope of the claims appended hereto.

What is claimed is:

1. A waveform generating system, which comprises:
   (a) means for generating waveforms during a plurality of time periods, each including sub-intervals,
   (b) waveform generation control means connected to said waveform generating means for defining the characteristics of the output waveform during each sub-interval,
   (c) timing means connected to said waveform generation control means for defining the periods and sub-intervals,
   (d) means for entering information into the system to define the periods, sub-intervals and characteristics of the output waveform, and
   (e) system control means connected to said information entering means, timing means and waveform generation means.

2. The waveform generating system of claim 1 in which said timing means including two sets of timing circuits which alternatively produce period and sub-interval defining signals during successive time periods, conditioning of the set of timing circuits not producing the defining signals to produce defining signals during a succeeding period in which the other set of the timing circuits is producing the defining signals.

3. The waveform generating system of claim 1 in which the time periods and sub-intervals are defined from selectively gated signals produced by a fundamental clock frequency generator and two parallel sets of counters for dividing the frequency produced by the frequency generator.

4. The waveform generating system of claim 1 in which the output waveforms are programmable with respect to voltage level, current and duration for each sub-interval.

5. The waveform generating system of claim 4 additionally comprising:
(f) response input signal means for receiving response waveforms from a biological sample to which the output waveforms from the system are supplied, and
(g) means for altering the characteristics of output waveforms during a subsequent time interval on the basis of the response waveforms.

6. A programmable system for generating electrical pulses to be supplied to a biological sample, which comprises:
(a) a fundamental clock frequency generation circuit,
(b) a plurality of frequency division circuits in first and second sets connected to an output of said fundamental frequency generation circuit,
(c) a period timing circuit connected to an output of each frequency division circuit in the first set and responsive to output signals from said first set frequency division circuits selectively to define given periods of time,
(d) a sub-interval timing circuit connected to an output of each frequency division circuit in said second set and responsive to output signals from said second set frequency division circuits selectively to define sub-intervals of time in each period defined by said period timing circuit,
(e) variable duration electrical signal generation means,
(f) means for storing information identifying period and sub-interval duration and signal characteristics desired during the sub-intervals of the periods, and
(g) control means responsive to the stored information and connected to the variable electrical signal generation means for generating signals in each period during the sub-intervals defined by the sub-interval timing circuits in accordance with the information in said information storage means.

7. The programmable system of claim 6 in which said variable electrical signal generation means and said timing circuits are triggered by at least some common triggering signals simultaneously to make delays in said timing circuits transparent to a user.

8. The programmable system of claim 7 in which means is provided for adding in clock pulses which would otherwise be missed by said timing circuits.

9. The system of claim 6 additionally comprising a digital to analog converter connected to said variable duration electrical signal generation means for providing analog voltage levels during the sub-intervals.

10. The system of claim 9 further comprising an analog to digital feedback loop connected between said digital to analog converter and said variable duration electrical signal generating eans.

* * * * *